US012735390B2

(12) United States Patent
Hunt et al.

(10) Patent No.: US 12,735,390 B2
(45) Date of Patent: Sep. 15, 2026

(54) PYRYLIUM METHOD OF PREPARING PYRIMIDINE CYCLOHEXYL GLUCOCORTICOID RECEPTOR MODULATORS

(71) Applicant: Corcept Therapeutics Incorporated, Redwood City, CA (US)

(72) Inventors: Hazel Joan Hunt, West Sussex (GB); Gary Patrick Reid, Redwood City, CA (US); Jeffrey Mark Dener, Redwood City, CA (US); Aaron Dumas, Hoddesdon (GB); Stephen Hyde, Hoddesdon (GB); Conor Marrett-Munro, Hoddesdon (GB); Shaun Stairs, Hoddesdon (GB); Christopher Wise, Hoddesdon (GB)

(73) Assignee: Corcept Therapeutics Incorporated, Redwood City, CA (US)

( * ) Notice: Subject to any disclaimer, the term of this patent is extended or adjusted under 35 U.S.C. 154(b) by 277 days.

(21) Appl. No.: 18/676,067

(22) Filed: May 28, 2024

(65) Prior Publication Data

US 2025/0011290 A1 Jan. 9, 2025

Related U.S. Application Data

(60) Provisional application No. 63/504,823, filed on May 30, 2023.

(51) Int. Cl.
*C07D 239/54* (2006.01)

(52) U.S. Cl.
CPC .................................. *C07D 239/54* (2013.01)

(58) Field of Classification Search
CPC ............................ C07D 239/54; C07D 401/04
See application file for complete search history.

(56) References Cited

U.S. PATENT DOCUMENTS 6,852,719 B2 2/2005 Liu et al.
7,576,076 B2 8/2009 Clark et al.
7,799,782 B2 9/2010 Munson et al.
8,173,664 B2 5/2012 Clark et al.
8,685,973 B2 4/2014 Clark et al.
8,906,917 B2 12/2014 Clark et al.
9,321,736 B2 4/2016 Clark et al.
9,622,979 B2 4/2017 Bhavarisetti et al.
10,238,659 B2 3/2019 Belanoff et al.
10,881,660 B2 1/2021 Belanoff et al.
11,542,238 B2 1/2023 Hunt et al.
11,548,856 B2 1/2023 Hunt et al.
11,760,731 B2 9/2023 Hunt et al.
2005/0245500 A1 11/2005 Roth et al.
2007/0155707 A1 7/2007 Dasse et al.
2010/0267643 A1 10/2010 Baron et al.
2013/0281324 A1 10/2013 Gouliaev et al.
2021/0238148 A1 8/2021 Hunt et al.
2021/0361651 A1 11/2021 Chia et al.
2021/0363112 A1 11/2021 Hunt et al.
2022/0220081 A1 7/2022 Dener et al.
2023/0183186 A1 6/2023 Hunt et al.
2023/0212128 A1 7/2023 Hunt et al.
2024/0083856 A1 3/2024 Hunt et al.

FOREIGN PATENT DOCUMENTS

EP 0037495 A1 10/1981
EP 0369627 A2 5/1990
EP 0722732 A1 7/1996
JP H06128238 A 5/1994
JP H1017555 A 1/1998
JP 2000271618 A 10/2000
WO 0244120 A1 6/2002
WO 03084935 A2 10/2003
WO 2010052445 A1 5/2010
WO 2012129074 A1 9/2012
WO 2016061195 A1 4/2016
WO 2019236487 A1 12/2019
WO 2021226258 A1 11/2021
WO 2021226260 A1 11/2021
WO 2022140293 A1 6/2022

OTHER PUBLICATIONS (2023) Eudragit® L 100, https://www.pharmaexcipients.com/product/eudragit-l-100/, 2 pages.
International Search Report and Written Opinion issued in related International Patent Application No. PCT/US2019/035229, mailed on Oct. 1, 2019, 10 pages.
International Search Report and Written Opinion issued in related International Patent Application. No. PCT/US2005/023675, mailed on Dec. 13, 2005, 11 pages.
International Search Report and Written Opinion issued in related International Patent Application. No. PCT/US2012/029376, mailed on Jun. 27, 2012, 8 pages.
International Search Report and Written Opinion received for PCT Application No. PCT/US2021/030923, mailed on Aug. 18, 2021, 11 pages.
International Search Report and Written Opinion received for PCT Application No. PCT/US2021/030925, mailed on Aug. 20, 2021, 14 pages.
International Search Report and Written Opinion received for PCT Application No. PCT/US2021/064428, mailed on Apr. 4, 0222, 16 pages.
Ali et al. (Apr. 2, 2004) "Novel N-Arylpyrazolo[3,2-c]-Based Ligands for the Glucocorticoid Receptor: Receptor Binding and in Vivo Activity", Journal of Medicinal Chemistry, 47(10):2441-2452.
Baptista, T. (Jul. 1999) "Body Weight Gain Induced by Antipsychotic Drugs: Mechanisms and Management", Acta Psychiatr Scand, 100(1):3-16.

(Continued)

*Primary Examiner* — Shawquia Jackson
(74) *Attorney, Agent, or Firm* — Mintz, Levin, Cohn, Ferris, Glovsky and Popeo, P.C.

(57) ABSTRACT

The present invention provides methods of preparing pyrimidine cyclohexyl glucocorticoid receptor modulators, methods of preparing intermediates of pyrimidine cyclohexyl glucocorticoid receptor modulators, and pyridinium compounds.

19 Claims, 1 Drawing Sheet

(56) References Cited

OTHER PUBLICATIONS

Bertagna et al. (Jul. 1984) "The New Steroid Analog RU 486 Inhibits Glucocorticoid Action in Man", The Journal of Clinical Endocrinology and Metabolism, 59(1):25-28.
Bhuyan et al. (1998) "Studies on Uracils: Synthesis of Novel Uracil Analogues via 1,5- and 1,6-Intramolecular Cycloaddition Reactions", XP002355359; Database CA 'Online'; Chemical Abstracts Service, Columbus, OH, US; Database Accession No. 598911.
Bledsoe et al. (Jul. 12, 2002) "Crystal Structure of the Glucocorticoid Receptor Ligand Binding Domain Reveals a Novel Mode of Receptor Dimerization and Coactivator Recognition", Cell, 110(1):93-105.
Brophy et al. (Jan. 1983) "Bioavailability of Oral Dexamethasone During High Dose Steroid Therapy in Neurological Patients", European Journal of Clinical Pharmacology, 24:103-108.
Butreddy, Arun (Aug. 2022) "Hydroxypropyl Methylcellulose Acetate Succinate as an Exceptional Polymer for Amorphous Solid Dispersion Formulations: A Review from Bench to Clinic", European Journal of Pharmaceutics and Biopharmaceutics, 177:289-307.
Cadepond et al. (1997) "RU486 (mifepristone): Mechanisms of Action and Clinical Uses", Annual Review of Medicine, 48:129-156.
Deshmukh et al. (1998) "Efficient Method for Deamination of Aminopyrimidines", National Academy Science Letters (India), 21(7-8):247-249.
Dorwald, Florencio Z. (2005) "Side Reactions in Organic Synthesis: A Guide to Successful Synthesis Design", Wiley-VCH, 390 pages.
Eyles et al. (Jul. 1997) "Oral Delivery and Fate of Poly(Lactic Acid) Microsphere- Encapsulated Interferon in Rats", Journal of Pharmacy and Pharmacology, 49(7):669-674.
Fotherby, K. (Aug. 1996) "Bioavailability of Orally Administered Sex Steroids Used in Oral Contraception and Hormone Replacement Therapy", Contraception, 54(2):59-69.
Fukazawa et al. (1998) "6-Amino-5-Methyluracil Derivativies and Their Use as Thymidine Phosphorylase Inhibitors and Neovascularization Inhibitors", XP002355358; Database CA 'Online'; Chemical Abstracts Service, Columbus, OH, US; Database Accession No. :59356, 4 pages.
Gao et al. (Jun. 1995) "Controlled Release of a Contraceptive Steroid from Biodegradable and Injectable Gel Formulations: In Vitro Evaluation", Pharmaceutical Research, 12(6):857-863.
Groning et al. (May 1996) "Threedimensional Solubility Parameters and Their Use in Characterising the Permeation of Drugs Through the Skin", Pharmazie, 51(5):337-341.
Hidalgo-Aragones et al. (Aug. 1996) "Pharmacokinetics of oestrone-3-O-sulphamate", The Journal of Steroid Biochemistry and Molecular Biology, 58(5-6):611-617.
Hilton et al. (Jul. 1993) "Use of Hydroxypropyl Methylcellulose Acetate Succinate in an Enteric Polymer Matrix to Design Controlled-release Tablets of Amoxicillin Trihydrate", Journal of Pharmaceutical Sciences, 82(7):737-743.
Hunt et al. (2012) "Discovery of a Novel Non-steroidal GR Antagonist With in Vivo Efficacy in the Olanzapine-induced Weight Gain Model in the Rat", Bioorganic & Medicinal Chemistry Letters, 22(24):7376-7380.
Johnson et al. (Sep. 1995) "Permeation of Steroids through Human Skin", Journal of Pharmaceutical Sciences, 84(9):1144-1146.
Koorneef et al. (2018) "Selective Glucocorticoid Receptor Modulation Prevents and Reverses Nonalcoholic Fatty Liver Disease in Male Mice", Endocrinology, 159(12):3925-3936.
Lee et al. (Apr. 2020) "Reversal of Antipsychotic-induced Weight Gain in Rats with Miricorilant, A Selective Glucocorticoid Receptor (Gr) Modulator", American Psychiatric Association Annual Meeting, 1 page.
Minto et al. (Apr. 1, 1997) "Pharmacokinetics and Pharmacodynamics of Nandrolone Esters in Oil Vehicle: Effects of Ester, Injection Site and Injection Volume", The Journal of Pharmacology and Experimental Therapeutics, 281(1):93-102.
Nguyen et al. (Sep. 1, 2017) "A Mixed Glucocorticoid/mineralocorticoid Receptor Modulator Dampens Endocrine and Hippocampal Stress Responsivity in Male Rats", Physiology & Behavior, 178:82-92.
Rao, K. Paduranga (1995) "Recent Developments of Collagen-Based Materials for Medical Applications and Drug Delivery Systems", Journal of Biomaterials Science, Polymer Edition, 7(7):623-645.
Rohatagi et al. (1995) "Pharmacokinetic and Pharmacodynamic Evaluation of Triamcinolone Acetonide After Intravenous, Oral, and Inhaled Administration", Journal of Clinical Pharmacology, 35(12):1187-1193.
Rohatagi et al. (Sep. 1, 1995) "Pharmacokinetic Interaction Between Endogenous Cortisol and Exogenous Corticosteroids", Die Pharmazie, 50(9):610-613.
Teutsch et al. (Nov. 1, 1991) "Design of Ligands for the Glucocorticoid and Progestin Receptors", Biochemical Society Transactions, 19(4):901-908.
Tjwa, M.K. (1995) "Budesonide Inhaled Via Turbuhaler: A More Effective Treatment for Asthma than Beclomethasone Dipropionate Via Rotahaler", Annals of Allergy, Asthma & Immunology, 75(2):107-111.
Turner et al. (Oct. 1, 2005) "Structure of the glucocorticoid receptor (NR3C1) gene 5' untranslated region: identification, and tissue distribution of multiple new human exon 1", Journal of Molecular Endocrinology, 35(2):283-292.
Umbricht et al. (Sep. 1994) "Clozapine and Weight Gain", The Journal of Clinical Psychiatry, 55(Suppl B):157-160.

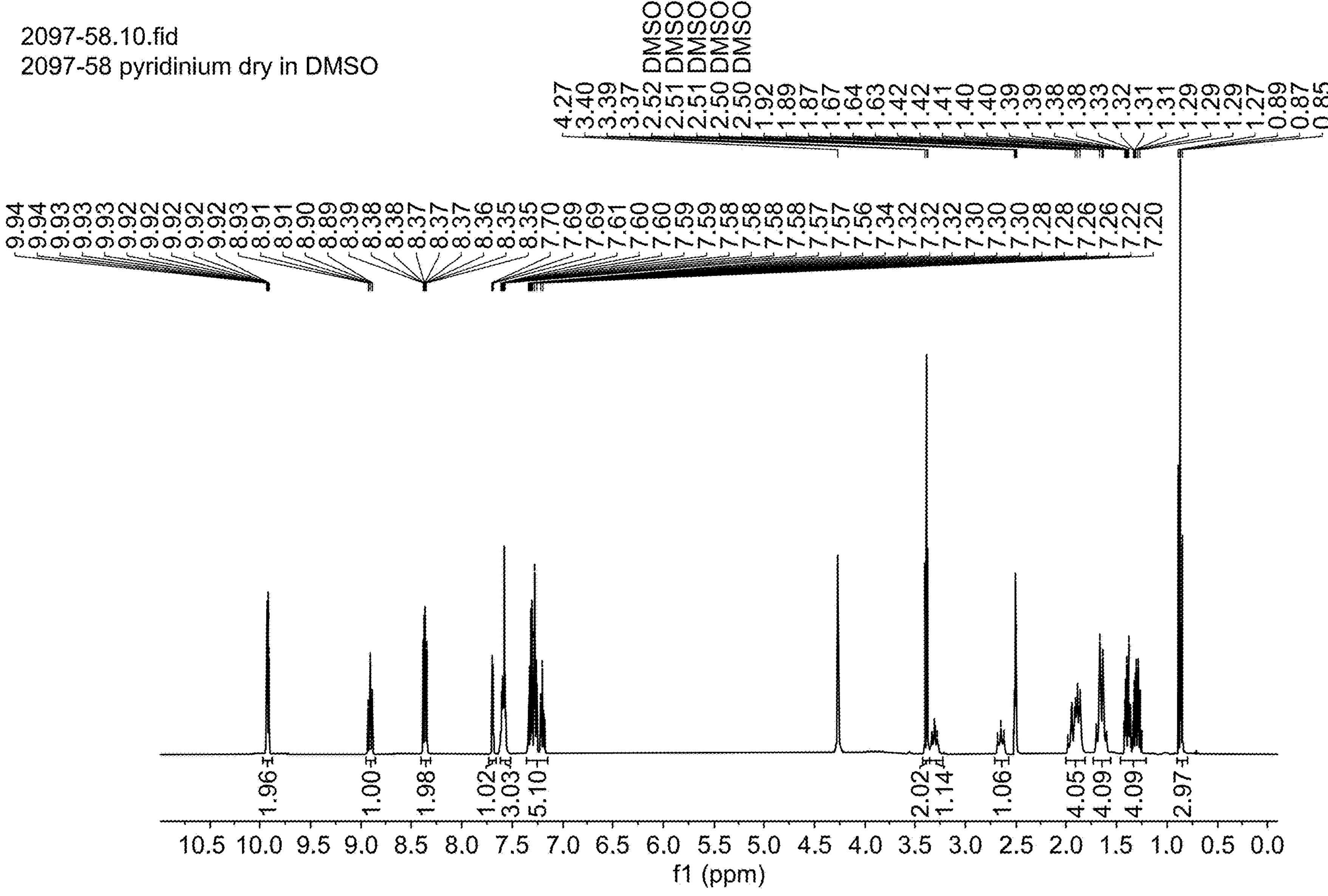
2097-58.10.fid
2097-58 pyridinium dry in DMSO
4.27
3.40
3.39
3.37
2.52 DMSO
2.51 DMSO
2.51 DMSO
2.50 DMSO
2.50 DMSO
1.92
1.89
1.87
1.67
1.64
1.63
1.42
1.42
1.41
1.40
1.40
1.39
1.39
1.38
1.38
1.33
1.32
1.31
1.31
1.29
1.29
1.29
1.27
0.89
0.87
0.85
9.94
9.94
9.93
9.93
9.93
9.92
9.92
9.92
9.92
9.92
8.93
8.91
8.91
8.90
8.89
8.39
8.38
8.38
8.37
8.37
8.37
8.36
8.35
8.35
7.70
7.69
7.69
7.61
7.60
7.60
7.59
7.59
7.58
7.58
7.58
7.58
7.57
7.57
7.56
7.34
7.32
7.32
7.32
7.30
7.30
7.30
7.28
7.28
7.26
7.26
7.22
7.20
1.96
1.00
1.98
1.02
3.03
5.10
2.02
1.14
1.06
4.05
4.09
4.09
2.97
10.5 10.0 9.5 9.0 8.5 8.0 7.5 7.0 6.5 6.0 5.5 5.0 4.5 4.0 3.5 3.0 2.5 2.0 1.5 1.0 0.5 0.0
f1 (ppm)

PYRYLIUM METHOD OF PREPARING PYRIMIDINE CYCLOHEXYL GLUCOCORTICOID RECEPTOR MODULATORS

CROSS-REFERENCES TO RELATED APPLICATIONS

This application claims the benefit of priority to U.S. Provisional Patent Application No. 63/504,823, filed 30 May 2023, the entirety of which is incorporated herein by reference.

BACKGROUND

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these include the ligand binding domain, GR-beta is unable to bind ligand, is constitutively localized in the nucleus, and is transcriptionally inactive. The GR is also known as the GR-II.

The biologic effects of cortisol, including those caused by hypercortisolemia, can be modulated at the GR level using receptor modulators, such as agonists, partial agonists and antagonists. Several different classes of agents are able to inhibit the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) J. Clin. Endocrinol. Metab. 59:25). Mifepristone binds to the GR with high affinity, with a dissociation constant (Kd) of 10-9 M (Cadepond (1997) Annu. Rev. Med. 48:129).

In addition to cortisol, the biological effects of other steroids can be modulated at the GR level using receptor modulators, such as agonists, partial agonists and antagonists. When administered to subjects in need thereof, steroids can provide both intended therapeutic effects, e.g., by stimulating glucocorticoid receptor transrepression, as well as negative side effects, e.g. by chronic glucocorticoid receptor transactivation. Miricorilant (CORT118335) is another such glucocorticoid receptor modulator compound, and has been described previously in PCT Publication No. WO 2012/129074, and U.S. Pat. No. 8,685,973. What is needed in the art are new methods of preparing miricorilant having lower impurity content. Surprisingly, the present invention meets these and other needs.

BRIEF SUMMARY OF THE INVENTION

In one embodiment, the present invention provides a method of preparing a compound of Formula I:

(I)

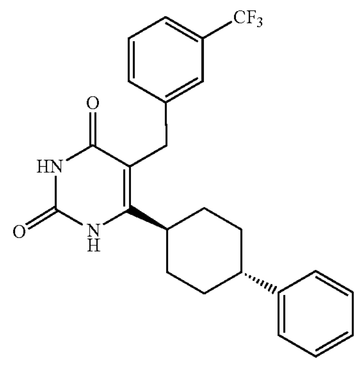

the method comprising:

(a) forming a first reaction mixture comprising a first solvent, a strong acid, and a compound of Formula VII:

(VII)

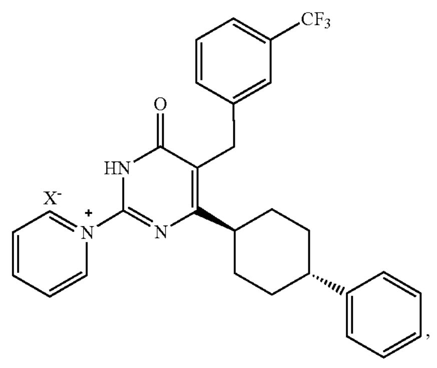

under conditions suitable to prepare the compound of Formula I, wherein counterion $X^-$ is tetrafluoroborate, chloride, bromide, tetrachloroferrate, pentachlorostannate, hexafluorophosphate, butyltriphenylborate, or tetrakis(4-methoxyphenyl)borate.

In another embodiment, the present invention provides a method of preparing a compound of Formula VII:

(VII)

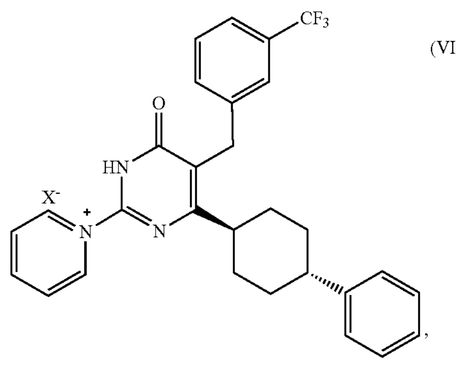

comprising (b) forming a second reaction mixture comprising a pyrylium salt:

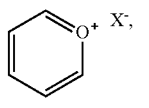

a second solvent and a compound of Formula II, or a hydrate thereof:

(II)

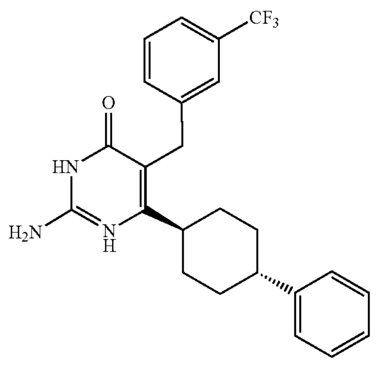

under conditions suitable to prepare the compound of Formula VII, wherein counterion $X^-$ is $BF_4^-$.

In another embodiment, the present invention provides a compound of Formula VII:

(VII)

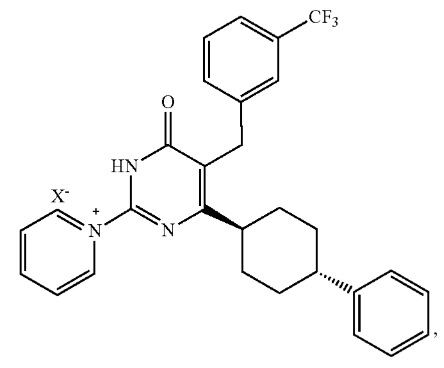

wherein counterion $X^-$ is tetrafluoroborate, chloride, bromide, tetrachloroferrate, pentachlorostannate, hexafluorophosphate, butyltriphenylborate, or tetrakis (4-methoxyphenyl)borate.

BRIEF SUMMARY OF THE DRAWINGS

FIG. 1 shows the proton NMR for the compound of Formula VII.

DETAILED DESCRIPTION OF THE INVENTION

I. General

The present disclosure describes methods of preparing 6-((1r,4r)-4-phenylcyclohexyl)-5-(3-(trifluoromethyl)benzyl)pyrimidine-2,4(1H,3H)-dione (Formula I), Example 6 of U.S. Pat. No. 8,685,973 via formation of a pyrylium intermediate from the compound of Formula II. The present disclosure also describes new intermediates.

II. Definitions

"About" when referring to a value includes the stated value +/−10% of the stated value. For example, about 50% includes a range of from 45% to 55%, while about 10 equivalents includes a range of from 9 to 11 equivalents. Accordingly, when referring to a range, "about" refers to each of the stated values +/−10% of the stated value of each end of the range. For instance, a ratio of from about 1 to about 10 (w/w) includes a range of from 0.9 to 11.

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, 1,4-dioxane, tetrahydrofuran, diethyl ether, acetone, ethyl acetate, N,N-dimethylformamide, dimethylacetamide, acetonitrile and dimethyl sulfoxide. Representative non-polar solvents include alkanes (pentanes, hexanes, etc.), cycloalkanes (cyclopentane, cyclohexane, etc.), benzene, and toluene. Other solvents are useful in the present invention.

"Acid" refers to a compound capable of donating a proton (a Bronsted-Lowry acid) or capable of accepting an electron pair (a Lewis acid). Representative acids include, but are not limited to, hydrochloric acid, sulfuric acid, formic acid, acetic acid, propanoic acid, butyric acid, hexanoic acid, octanoic acid, trifluoroacetic acid, tetrafluoroboric acid ($HBF_4$), etc.

"Strong acid" refers to an acid that easily dissociates, which is often represented by a $pK_a$ less than −1 in water. Representative strong acids include, but are not limited to, hydrochloric acid, hydrobromic acid, hydroiodic acid, nitric acid, sulfuric acid, and perchloric acid.

"Hydrate" refers to a compound that is complexed to at least one water molecule. The compounds of the present invention can be complexed with from 1 to 10 water molecules.

"Cooling" refers to applying cooling means to the reaction mixture to decrease the temperature of the reaction mixture by at least 1 degree Celsius. For example, cooling can include, but is not limited to, decreasing the temperature of the reaction mixture to or below room temperature.

"Heating" refers to applying heat to the reaction mixture to increase the temperature of the reaction mixture by at least 1 degree Celsius. For example, heating can include, but is not limited to, raising the temperature of the reaction mixture to room temperature, or to the reflux or boiling temperature of the reaction mixture, or to a temperature between room temperature and the reflux or boiling temperature of the reaction mixture.

"Room temperature" is the range of air temperatures generally considered to be suitable for human occupancy, or between about 15 degrees Celsius (59 degrees Fahrenheit) and 25 degrees Celsius (77 degrees Fahrenheit).

"Crystalline seed" refers to a seed crystal of the target crystalline form to be prepared.

III. Pyrylium Method of Preparing Formula I

The present invention provides methods for the preparation of 6-((1r,4r)-4-phenylcyclohexyl)-5-(3-(trifluoromethyl)benzyl)pyrimidine-2,4(1H,3H)-dione, the compound of Formula I:

(I)

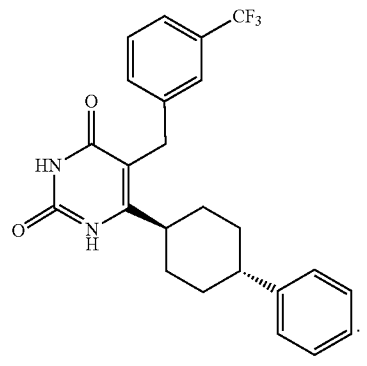

The compound of Formula I was originally disclosed as Example 6 in U.S. Pat. No. 8,685,973.

A. Preparation of Formula I from Formula VII

In some embodiments, the present invention provides a method of preparing a compound of Formula I:

(I)

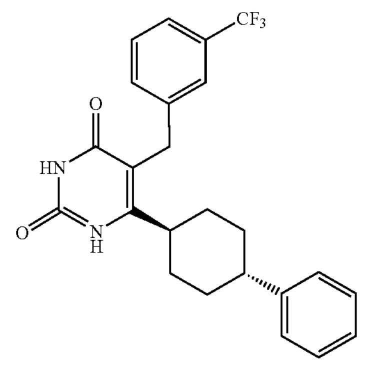

the method comprising: (a) forming a first reaction mixture comprising a first solvent, a strong acid, and a compound of Formula VII:

(VII)

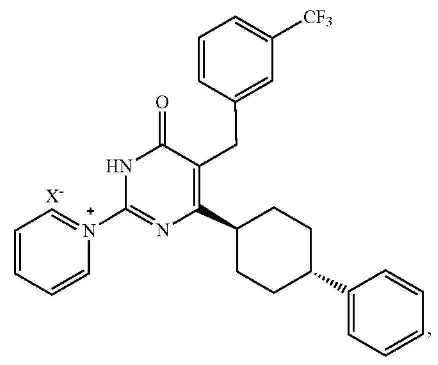

under conditions suitable to prepare the compound of Formula I, wherein counterion $X^-$ is tetrafluoroborate, chloride, bromide, tetrachloroferrate, pentachlorostannate, hexafluorophosphate, butyltriphenylborate, or tetrakis(4-methoxyphenyl)borate.

Any suitable solvent can be used as the first solvent in the first reaction mixture of the present invention. Representative solvents include, but are not limited to, a polar aprotic solvent, a polar protic solvent, or a non-polar solvent. In some embodiments, the method of preparing the compound of Formula I includes the method wherein the first solvent comprises acetic acid, propionic acid, butyric acid, valeric acid, caproic acid, isobutyric acid, isovaleric acid, 4-methylvaleric acid, or 2-ethylcaproic acid. In some embodiments, the method of preparing the compound of Formula I includes the method wherein the first solvent comprises acetic acid, propionic acid, or butyric acid. In some embodiments, the method of preparing the compound of Formula I includes the method wherein the first solvent comprises acetic acid.

Any strong acid can be used as the strong acid in the first reaction mixture of the present invention. Representative strong acids include, but are not limited to, organic acids and inorganic acids. In some embodiments, the method of preparing the compound of Formula I includes the method wherein the strong acid comprises trifluoroacetic acid, trichloroacetic acid, ethane-1,2-disulfonic acid, naphthalene-2-sulfonic acid, naphthalene-1,5-disulfonic acid, hydrofluoric acid, hydrochloric acid, hydrobromic acid, hypochlorous acid, chloric acid, perchloric acid, sulfuric acid, nitric acid, phosphoric acid, methanesulfonic acid, ethanesulfonic acid, benzenesulfonic acid, p-toluenesulfonic acid, trifluoromethanesulfonic acid, camphorsulfonic acid, or combinations thereof. In some embodiments, the method of preparing the compound of Formula I includes the method wherein the strong acid comprises hydrochloric acid. In some embodiments, the method of preparing the compound of Formula I includes the method wherein the strong acid comprises concentrated hydrochloric acid. Concentrated hydrochloric acid can have a normality of about 12N and a concentration of about 12M. In some embodiments, the method of preparing the compound of Formula I includes the method wherein the strong acid comprises about 37% (w/w) hydrochloric acid.

The strong acid can be present in any suitable amount to the compound of Formula VII. For example, the strong acid can be present in an amount of from 1 to 10 molar equivalents to the compound of Formula VII, or from 1 to 8, from 2 to 7, from 4 to 6, from 4.5 to 5.5, from 4.6 to 5.4, from 4.7 to 5.3, from 4.8 to 5.2, or from 4.9 to 5.1 molar equivalents to the compound of Formula VII. Representative amounts of the strong acid include, but are not limited to, about 1.0 molar equivalent to the compound of Formula VII, or about 2.0, 3.0, 3.5, 4.0, 4.5, 4.6, 4.7, 4.8, 4.9, 5.0, 5.1, 5.2, 5.3, 5.4, 5.5, 6.0, 6.5, 7.0, 8.0, 9.0, or about 10 molar equivalents to the compound of Formula VII. In some embodiments, the method of preparing the compound of Formula I includes the method wherein the strong acid is present in an amount from 4 to 6 molar equivalents to the compound of Formula VII. In some embodiments, the method of preparing the compound of Formula I includes the method wherein the strong acid is present in an amount of about 5 molar equivalents to the compound of Formula II.

Any suitable counterion can be used as the counterion $X^-$ of the compound of Formula VII in the first reaction mixture of the present invention. Representative counterions $X^-$ include tetrafluoroborate, chloride, bromide, tetrachloroferrate, pentachlorostannate, hexafluorophosphate, butyltriphenylborate, or tetrakis(4-methoxyphenyl)borate. In some embodiments, the method of preparing the compound of Formula I includes the method wherein counterion $X^-$ is $BF_4^-$.

In some embodiments, the method of preparing the compound of Formula I includes the method wherein the compound of Formula VII has the structure:

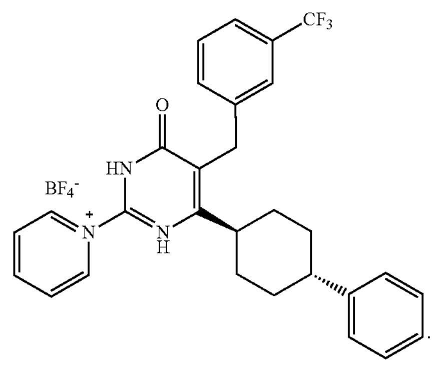

In some embodiments, the method of preparing the compound of Formula I includes the method comprising: (a) forming the first reaction mixture comprising the compound of Formula VII, acetic acid, and concentrated hydrochloric acid, under conditions suitable to prepare the compound of Formula I.

B. Preparation of Formula VII from Formula II

The compound of Formula VII, a salt comprising 1-(6-oxo-4-((1r,4r)-4-phenylcyclohexyl)-5-(3-(trifluoromethyl)benzyl)-1,6-dihydropyrimidin-2-yl)pyridin-1-ium:

(VII)

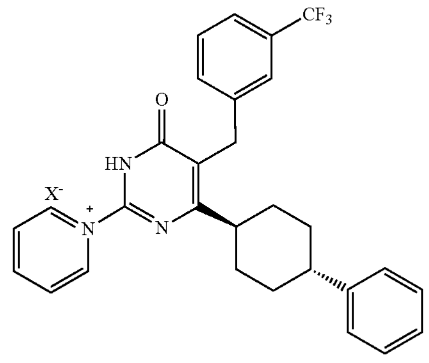

can be prepared by a variety of methods.

In some embodiments, the present invention provides a method of preparing a compound of Formula VII:

(VII)

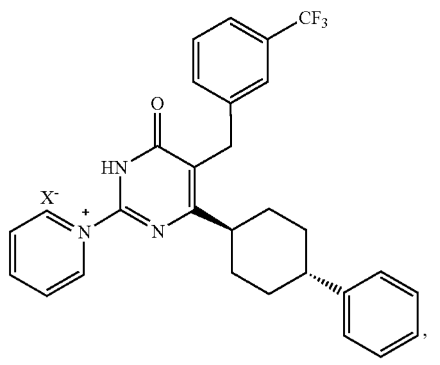

comprising (b) forming a second reaction mixture comprising a pyrylium salt:

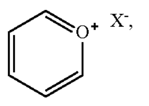

a second solvent and a compound of Formula II, or a hydrate thereof:

(II)

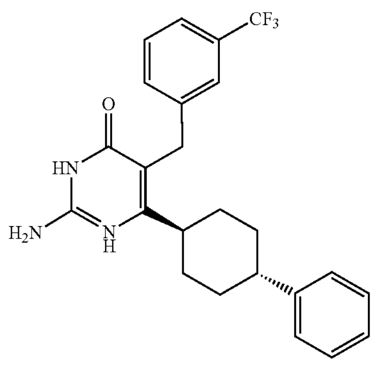

under conditions suitable to prepare the compound of Formula VII, wherein counterion $X^-$ is $BF_4^-$.

In some embodiments, the method of preparing the compound of Formula VII includes the method wherein the pyrylium salt is pyrylium tetrafluoroborate having the structure:

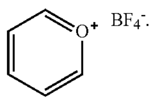

The pyrylium salt can be present in any suitable amount to the compound of Formula II. For example, the pyrylium salt can be present in an amount of from 0.1 to 10 molar equivalents to the compound of Formula II, or from 0.2 to 5, from 0.5 to 3, from 1 to 3, from 1 to 1.5, or from 1 to 1.2 molar equivalents to the compound of Formula II. Representative amounts of the pyrylium salt include, but are not limited to, about 0.5 molar equivalents to the compound of Formula II, or about 0.6, 0.7, 0.8. 0.9, 1.0, 1.1, 1.2, 1.3, 1.4, 1.5, 2.0, 2.5, 3.0, 4.0, 5.0, 6.0, 7.0, 8.0, 9.0, or 10 molar equivalents to the compound of Formula II. In some embodiments, the method of preparing the compound of Formula VII includes the method wherein the pyrylium salt is present in an amount of from 1 to 3 molar equivalents to the compound of Formula II. In some embodiments, the method of preparing the compound of Formula VII includes the method wherein the pyrylium salt is present in an amount of about 1.1 molar equivalents to the compound of Formula II.

Any suitable solvent can be used as the second solvent in the second reaction mixture of the present invention. Representative second solvents include, but are not limited to, polar protic solvents, polar aprotic solvents, and non-polar solvents. In some embodiments, the method of preparing the compound of Formula VII includes the method wherein the second solvent comprises methanol, ethanol, n-propanol, isopropanol, n-butanol, t-butanol, 1-pentanol, 2-pentanol, 3-pentanol, 2-methyl-1-propanol, 1-methoxy-2-propanol, 4-methyl-2-pentanol, 1-hexanol, 2-hexanol, 1-octanol, or 2-octanol, or combinations thereof. In some embodiments, the method of preparing the compound of Formula VII includes the method wherein the second solvent comprises n-propanol or n-butanol. In some embodiments, the method of preparing the compound of Formula VII includes the method wherein the second solvent comprises n-butanol.

The compound of Formula II can be the free base form or the hydrate form. In some embodiments, the compound of Formula II is the free base. In some embodiments, the compound of Formula II is the hydrate. The compound of Formula II can be any suitable hydrate. For example, the compound of Formula II can be a monohydrate, dihydrate, trihydrate, or tetrahydrate. In some embodiments, the compound of Formula II is a monohydrate.

In some embodiments, the method of preparing the compound of Formula VII includes the method wherein the compound of Formula II is the monohydrate form:

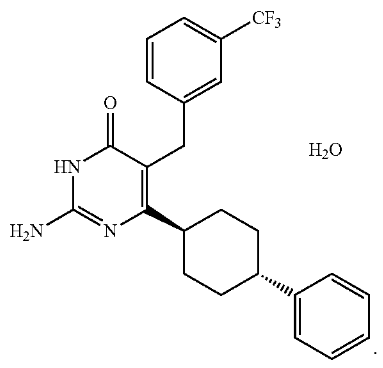 [SMILES: Nc1nc([C@H]2CC[C@H](c3ccccc3)CC2)c(Cc2cccc(C(F)(F)F)c2)c(=O)[nH]1 ; O]

In some embodiments, the method of preparing the compound of Formula VII includes the method comprising (b) forming the second reaction mixture comprising pyrylium tetrafluoroborate in an amount of about 1.1 molar equivalents to the compound of Formula II, n-butanol, and the compound of Formula II, under conditions suitable to prepare the compound of Formula VII.

In some embodiments, the present invention provides a method of preparing a compound of Formula I, wherein the compound of Formula VII is prepared by the methods of the present invention.

In some embodiments, the method of preparing the compound of Formula I includes the method comprising: (b) forming the second reaction mixture comprising pyrylium tetrafluoroborate in an amount of about 1.1 molar equivalents to the compound of Formula II, n-butanol, and the compound of Formula II, under conditions suitable to prepare the compound of Formula VII; and (a) forming the first reaction mixture comprising the compound of Formula VII, acetic acid, and concentrated hydrochloric acid, under conditions suitable to prepare the compound of Formula I.

C. Pyrylium Intermediate Compounds

The present invention provides compounds of Formula VII. In some embodiments, the present invention provides a compound of Formula VII:

(VII)

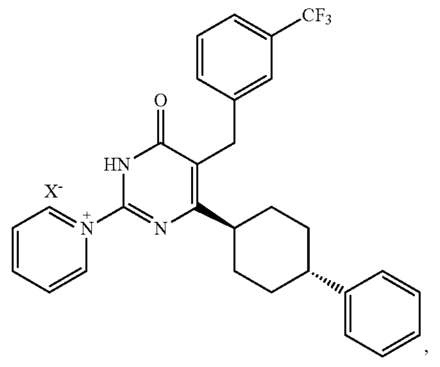

wherein counterion $X^-$ is tetrafluoroborate, chloride, bromide, tetrachloroferrate, pentachlorostannate, hexafluorophosphate, butyltriphenylborate, or tetrakis(4-methoxyphenyl)borate.

In some embodiments, the compound of Formula VII has the structure:

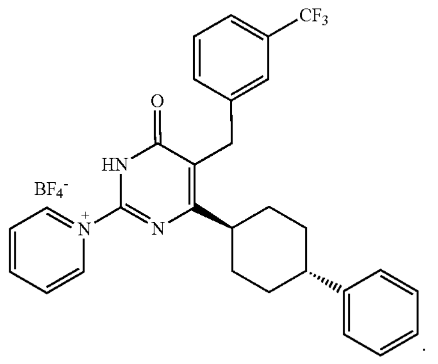

The compound of Formula VII is named 1-(6-oxo-4-((1r,4r)-4-phenylcyclohexyl)-5-(3-(trifluoromethyl)benzyl)-1,6-dihydropyrimidin-2-yl)pyridin-1-ium tetrafluoroborate using IUPAC nomenclature.

IV. Examples

The following acronyms and abbreviations are used in the methods below:

| | |
|---|---|
| AcOH | Acetic acid |
| aq | Aqueous |
| atm | Atmospheric pressure |
| ° C. | Degree Celsius |
| DBU | 1,8-Diazabicyclo[5.4.0]undec-7-ene |
| DCM | Dichloromethane |
| DMF | N,N-Dimethylformamide |
| DMAP | N,N-Dimethylaminopyridine/4-(Dimethylamino)pyridine |
| DSC | Differential Scanning Calorimetry |
| EDC | 1-Ethyl-3-(3-dimethylaminopropyl)carbodiimide |
| eq | Equivalent |
| GF | Glass microfiber filter paper |
| g | Gram |
| HCl | Hydrochloric acid |
| hdpe | High density polyethylene |
| HPLC | High-performance Liquid Chromatography |
| KF | Karl Fischer titration |
| L | Liter |
| LCAP | HPLC Area Percent |
| LCWP | HPLC Weight Percent |
| M | Molar |
| MeCN | Acrylonitrile |
| MeOH | Methanol |
| mins | Minutes |
| mL | Milliliter |
| nBuOH | butan-1-ol |
| NMP | N-Methyl-2-pyrrolidone |
| Pd-C | Palladium on carbon |
| $^1$H-NMR | Proton Nuclear Magnetic Resonance |
| ref std | Reference Standard |
| RT | Room Temperature |
| SM | Starting Material |
| T | Temperature |
| THF | Tetrahydrofuran |
| TMS | Tetramethylsilane |
| TG-DTA | Thermogravimetric Differential Thermal Analysis |
| vol | Volume |
| wrt | With respect to |
| Wt | Weight |
| XRPD | X-ray Powder Diffraction |

X-ray Powder Diffraction (XRPD). XRPD analyses were performed using a Panalytical Xpert Pro diffractometer equipped with a Cu X-ray tube and a Pixcel detector system. The samples were analyzed at ambient temperature in transmission mode and held between PVC films. The default XRPD program was used (range 3-40° 2θ, step size 0.013°, counting time 99 sec, ~22 min run time/counting time 49 sec for the Compound of Formula II and ~11 min run time/counting time 22 sec for the both Forms of the Compound of Formula VII Samples were spun at 60 rpm during data collection. XRPD patterns were sorted, manipulated using HighScore Plus 2.2c software.

Differential Scanning Calorimetry (DSC). DSC analyses were carried out on a Perkin Elmer Jade Differential Scanning Calorimeter. Accurately weighed samples were placed in gold pans and lid secured. Each sample was heated under nitrogen at a rate of 5° C./minute to a maximum of 200 or 300° C.

Thermogravimetric Differential Thermal Analysis (TG-DTA). Thermogravimetric (TG) analyses were carried out on a Mettler Toledo TGA/DSC 1 STAR$^e$ simultaneous thermal analysis instrument. Samples were placed in an aluminium sample pan, inserted into the TG furnace and accurately weighed. Under a stream of nitrogen at a rate of 10° C./minute, the heat flow signal was stabilized for one minute at 30° C., prior to heating to 300° C.

Proton Nuclear Magnetic Resonance Spectroscopy ($^1H$-NMR). Proton NMR analyses were performed on a 500 MHz Bruker AVANCE NEO instrument fitted with a Prodigy BBO CryoProbe. Samples were dissolved in the appropriate deuterated NMR solvent containing tetramethylsilane (TMS) as an internal standard, possessing an isotopic purity of ≥99.5 atom % D, then the solution of the sample was analyzed using 5 mm Virgin NMR tubes.

"Conditions suitable" for conducting the methods of the present invention include the time and temperature for conducting the methods, as defined below.

The reaction steps of the present invention can be performed for any suitable reaction time. For example, the reaction time can be for minutes, hours, or days. In some embodiments, the reaction time can be for several hours, such as at least eight hours. In some embodiments, the reaction time can be for several hours, such as at least overnight. In some embodiments, the reaction time can be for several days. In some embodiments, the reaction time can be for at least two hours. In some embodiments, the reaction time can be for at least eight hours. In some embodiments, the reaction time can be for at least several days. In some embodiments, the reaction time can be for about two hours, or for about 4 hours, or for about 6 hours, or for about 8 hours, or for about 10 hours, or for about 12 hours, or for about 14 hours, or for about 16 hours, or for about 18 hours, or for about 20 hours, or for about 22 hours, or for about 24 hours. In some embodiments, the reaction time can be for about 1 day, or for about two days, or for about three days, or for about four days, or for about five days, or for about six days, or for about a week, or for about more than a week.

The reaction steps of the present invention can be performed at any suitable reaction temperature. Representative temperatures include, but are not limited to, below room temperature, at room temperature, or above room temperature. Other temperatures useful in the methods of the present invention include from about −40° C. to about 65° C., or from about room temperature to about 40° C., or from about 40° C. to about 65° C., or from about 40° C. to about 60° C. In some embodiments, the reaction mixture can be at a temperature of about room temperature, or at a temperature of about 15° C., or at about 20° C., or at about 25° C. or at about 30° C., or at about 35° C., or at about 40° C., or at about 45° C., or at about 50° C., or at about 55° C., or at about 60° C., or at about 65° C.

Example 1. Preparation of 6-((1r,4r)-4-phenylcyclohexyl)-2-(1M-pyrylium-1-yl)-5-(3-(trifluoromethyl)benzyl)pyrimidin-4(3H)-one tetrafluoroboronate (Formula VII)

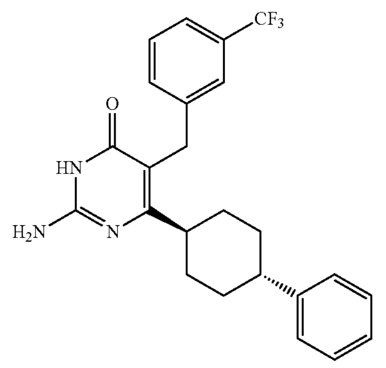

Formula II

-continued

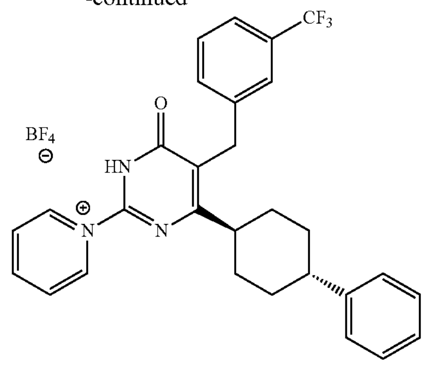

Formula VII

Formula II was prepared according to the methods described in WO2022/140293.

Formula II (33 g, 94 wt %, 72.6 mmol, 1 eq.) was slurried in nBuOH (42 vol., 1386 ml). The stream was concentrated to 35 vol. (1155 ml) under vacuum. The stream was transferred to an inerted jacketed vessel equipped with an overhead stirrer and treated with Pyrylium·$BF_4$ (11 g, 97.7 wt %, 65.3 mmol, 0.9 eq.). The contents were heated to 100° C. and aged for 2 hours. The reaction was analysed by HPLC, indicating 16.0 LCAP of Formula II still present.

The stream was distilled to 30 vol. under vacuum, nBuOH (5 vol., 165 ml) was added followed by Pyrylium·$BF_4$ (1.21 g, 7.25 mmol, 0.1 eq.). After aging at 100° C. for 1 hour, HPLC indicated 7.7 LCAP SM remaining. The stream was distilled to 30 vol. and nBuOH (5 vol., 165 ml) was added, followed by Pyrylium·$BF_4$ (0.61 g, 0.05 eq., 3.62 mmol). After a 1-hour age at 100° C., HPLC indicated that 5.6 LCAP of Formula II remained.

The stream was distilled to a final volume of 5 vol. (165 ml) and the resultant slurry was aged overnight. The liquor concentration of Formula VII was determined at 8.2 mg/ml. The product was isolated via filtration and the cake was washed with nBuOH (2×2 vol., 66 ml). The product was transferred to a vacuum oven and dried overnight at 50° C. A total of 39.1 g of Formula VII was isolated as a beige crystalline solid. m/z [M+H]: 490.30. $^{19}F$ NMR (DMSO-d6): −61.1, −148.3. The $^1H$ NMR (DMSO-d6) is provided in FIG. 1.

Example 2. Preparation of 6-((1r,4r)-4-phenylcyclohexyl)-5-(3-(trifluoromethyl)benzyl)pyrimidine-2,4 (1H,3H)-dione (Formula I)

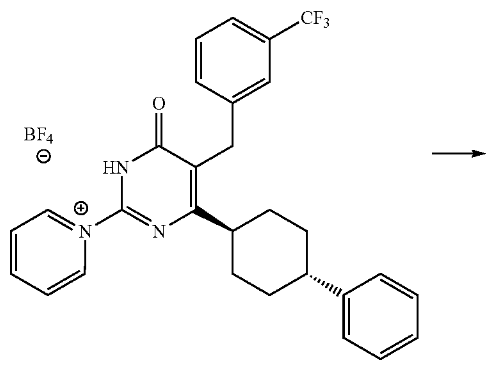

Formula VII

-continued

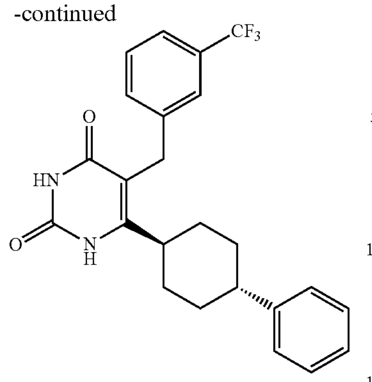

Formula I

Formula VII (72.2 g, 93.6 wt %, 117.1 mmol, 1.0 eq.) was charged to an inerted 1 L round-bottom flask fitted with an overhead stirrer. AcOH (8 vol., 578 ml) was added, and the contents were stirred. To the slurry was added cone HCl (~37%, 48.8 ml, 58.1 g, 585.5 mmol, 5 eq.). The contents were warmed to 70° C. and aged. The reaction was monitored by HPLC for extent of conversion.

After 3 hours the reaction was deemed complete and the contents were cooled to 20° C., over ~1 hour, during which time a slurry formed. To the slurry was added water (1 vol., 72 ml), drop-wise over ~1 hour. The slurry was aged for 30 mins and the liquor concentration of Formula I was determined as 2.8 mg/ml. The slurry was aged for a further 1 hour and the liquor loss dropped to 2.5 mg/ml. The product was isolated via filtration and the filter cake was washed sequentially with AcOH:water (8:1, 2×2 vol., 144 ml) and water (2×2 vol., 144 ml). The product was transferred to a vacuum oven and dried overnight at 50° C. CORT118335 (miricorilant) (52.8 g) was isolated as an off-white crystalline solid. 1H-NMR was consistent with Formula I standard, and product appeared to be an AcOH solvate.

Formula I (50 g, 89.7 wt %, 104.7 mmol, 1 eq.) was slurried in DCM (11 vol., 550 ml) in an inerted 1 L round-bottom flask equipped with an overhead stirrer. The slurry was warmed to 30° C., forming a solution. The solution was filtered through GF/A grade filter paper (coloured imps removed) and a line wash of DCM (1 vol., 50 ml) was conducted. The DCM streams were combined, and MeOH (3 vol., 150 ml) added. The solution was distilled to a final volume of 5 vol. (250 ml) at atmospheric pressure (T=~50° C.). To the stream was added MeOH (500 ml, 10 vol.) and the solution was seeded with authentic Formula I (0.1 wt %, 50 mg, 0.105 mmol), generating a mobile white slurry which thickened over time. The slurry was distilled to a final volume of 5 vol. (250 ml) under atmospheric pressure (T~60° C.), and the stream was treated with MeOH (500 ml, 10 vol.). The stream was distilled to a final volume of 5 vol. (250 ml), under atmospheric pressure (T~65° C.). The slurry was treated with MeOH (250 ml, 5 vol.) and the batch was allowed to cool to 20-25° C. over a period of two hours. A sample of the slurry was removed and analysed via XRPD confirming the correct polymorphic form had been generated. The liquor concentration of miricorilant was determined as 4.1 mg/ml and the product was isolated by filtration and the cake was washed with MeOH (2×1 vol., 50 ml). The product was transferred to a vacuum oven and dried overnight at 50° C. Pure Formula I was obtained as a white crystalline solid (42.4 g).

The characterization data of the title product matched those of Example 6 of U.S. Pat. No. 8,685,973, and Example 2 of U.S. Pat. No. 11,548,856.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a compound of Formula I:

(I)

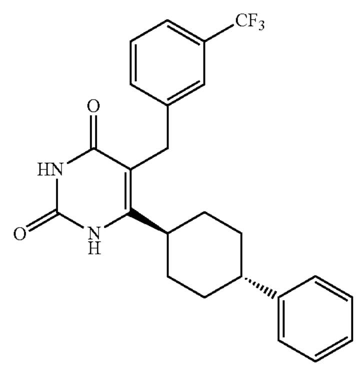

the method comprising:

(a) forming a first reaction mixture comprising a first solvent, a strong acid, and a compound of Formula VII:

(VII)

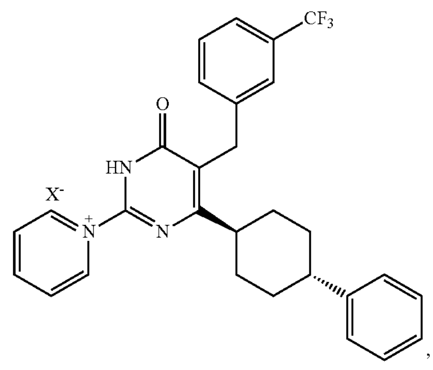

under conditions suitable to prepare the compound of Formula I, wherein counterion $X^-$ is tetrafluoroborate, chloride, bromide, tetrachloroferrate, pentachlorostannate, hexafluorophosphate, butyltriphenylborate, or tetrakis(4-methoxyphenyl)borate.

2. The method of claim 1, wherein the first solvent comprises acetic acid, propionic acid, butyric acid, valeric acid, caproic acid, isobutyric acid, isovaleric acid, 4-methylvaleric acid, or 2-ethylcaproic acid.

3. The method of claim 1, wherein the strong acid comprises trifluoroacetic acid, trichloroacetic acid, ethane-1,2-disulfonic acid, naphthalene-2-sulfonic acid, naphthalene-1,5-disulfonic acid, hydrofluoric acid, hydrochloric acid, hydrobromic acid, hypochlorous acid, chloric acid, perchloric acid, sulfuric acid, nitric acid, phosphoric acid, methanesulfonic acid, ethanesulfonic acid, benzenesulfonic acid, p-toluenesulfonic acid, trifluoromethanesulfonic acid, camphorsulfonic acid, or combinations thereof.

4. The method of claim 1, wherein the strong acid comprises hydrochloric acid.

5. The method of claim 1, wherein counterion $X^-$ is $BF_4^-$.

6. The method of claim 1, wherein the compound of Formula VII has the structure:

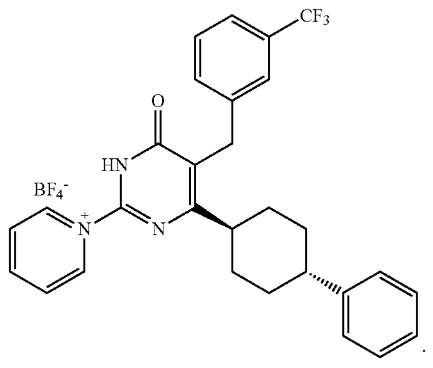

7. The method of claim 1, comprising:

(a) forming the first reaction mixture comprising the compound of Formula VII, acetic acid, and concentrated hydrochloric acid, under conditions suitable to prepare the compound of Formula I.

8. A method of preparing a compound of Formula VII:

(VII)

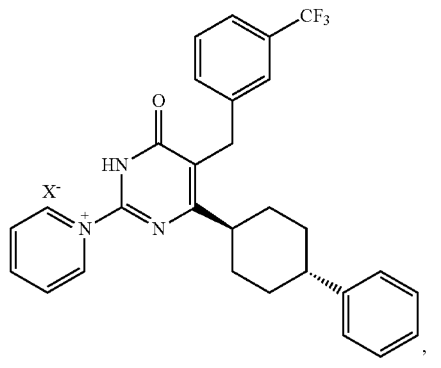

comprising (b) forming a second reaction mixture comprising a pyrylium salt:

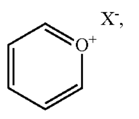

a second solvent and a compound of Formula II, or a hydrate thereof:

(II)

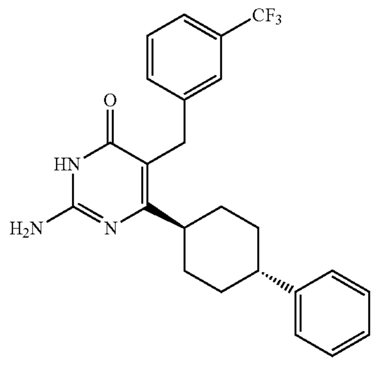

under conditions suitable to prepare the compound of Formula VII, wherein counterion $X^-$ is $BF_4^-$.

9. The method of claim 8, wherein the pyrylium salt is pyrylium tetrafluoroborate having the structure:

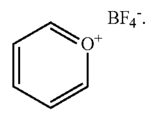

10. The method of claim 8, wherein the pyrylium salt is present in an amount of from 1 to 3 molar equivalents to the compound of Formula II.

11. The method of claim 8, wherein the pyrylium salt is present in an amount of about 1.1 molar equivalents to the compound of Formula II.

12. The method of claim 8, wherein the second solvent comprises methanol, ethanol, n-propanol, isopropanol, n-butanol, t-butanol, 1-pentanol, 2-pentanol, 3-pentanol, 2-methyl-1-propanol, 1-methoxy-2-propanol, 4-methyl-2-pentanol, 1-hexanol, 2-hexanol, 1-octanol, or 2-octanol, or combinations thereof.

13. The method of claim 8, wherein the second solvent comprises n-propanol or n-butanol.

14. The method of claim 8, wherein the compound of Formula II is the monohydrate form:

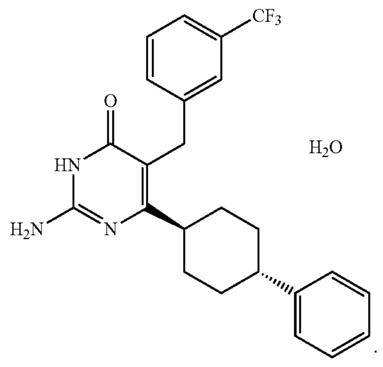 [SMILES: Nc1nc([C@H]2CC[C@H](c3ccccc3)CC2)c(Cc2cccc(C(F)(F)F)c2)c(=O)[nH]1 ; O]

15. The method of claim 8, comprising (b) forming the second reaction mixture comprising pyrylium tetrafluoroborate in an amount of about 1.1 molar equivalents to the compound of Formula II, n-butanol, and the compound of Formula II, under conditions suitable to prepare the compound of Formula VII.

16. The method of claim 1, wherein the compound of Formula VII is prepared by (b) forming a second reaction mixture comprising a pyrylium salt:

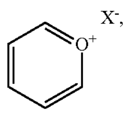

a second solvent and a compound of Formula II, or a hydrate thereof:

(II)

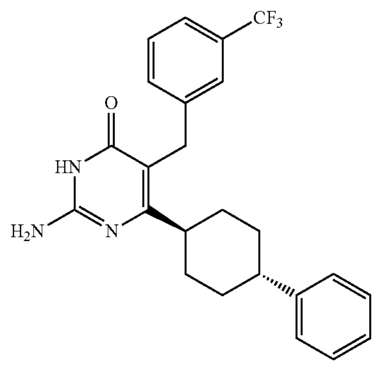

under conditions suitable to prepare the compound of Formula VII, wherein counterion $X^-$ is $BF_4^-$.

17. The method of claim 16, comprising:

(b) forming the second reaction mixture comprising pyrylium tetrafluoroborate in an amount of about 1.1 molar equivalents to the compound of Formula II, n-butanol, and the compound of Formula II, under conditions suitable to prepare the compound of Formula VII; and (a) forming the first reaction mixture comprising the compound of Formula VII, acetic acid, and concentrated hydrochloric acid, under conditions suitable to prepare the compound of Formula I.

18. A compound of Formula VII:

(VII)

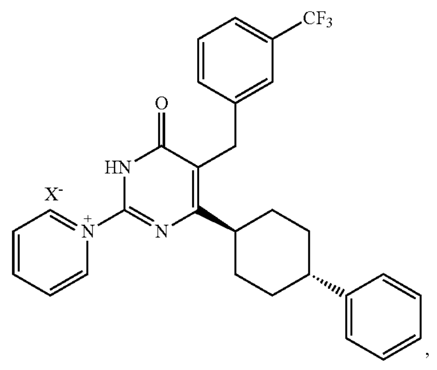

wherein counterion $X^-$ is tetrafluoroborate, chloride, bromide, tetrachloroferrate, pentachlorostannate, hexafluorophosphate, butyltriphenylborate, or tetrakis (4-methoxyphenyl)borate.

19. The compound of claim 18, wherein the compound of Formula VII has the structure:

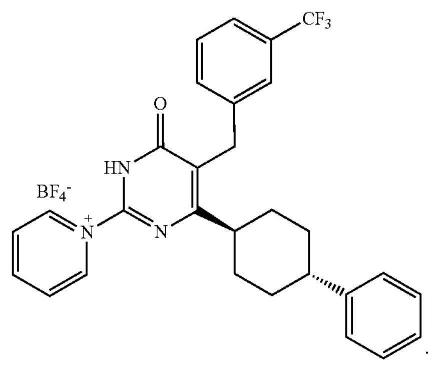

* * * * *